United States Patent [19]

Sherrod et al.

[11] 4,083,873
[45] Apr. 11, 1978

[54] NOVEL BISULFATE AND SULFATE SALTS OF BIS(2-AMINOETHYL) ETHER AND METHODS OF PREPARATION

[75] Inventors: Fred A. Sherrod, Freeport; Bobby R. Ezzell, Angleton, both of Tex.

[73] Assignee: The Dow Chemical Company, Midland, Mich.

[21] Appl. No.: 730,108

[22] Filed: Oct. 6, 1976

[51] Int. Cl.$^2$ .............................................. C07C 93/04
[52] U.S. Cl. .......................... 260/584 R; 260/458 R; 260/692
[58] Field of Search .............. 260/584 R, 458 R, 692, 260/614 R, 584 C

[56] References Cited

U.S. PATENT DOCUMENTS

| | | | |
|---|---|---|---|
| 711,565 | 10/1902 | Harris | 260/614 R |
| 749,078 | 1/1904 | Meyer | 260/614 R |
| 1,436,288 | 11/1922 | Plauson | 260/614 R |
| 1,873,538 | 8/1932 | Brown et al. | 260/614 R |

*Primary Examiner*—Daniel E. Wyman
*Assistant Examiner*—John J. Doll
*Attorney, Agent, or Firm*—Melvin William Barrow

[57] ABSTRACT

The title compounds correspond to formulas $O\text{-}(CH_2CH_2NH_3^\oplus)_2 \cdot 2HSO_4^\ominus$ and $)\text{-}(CH_2CH_2NH_3^\oplus)_2 \cdot SO_4^\ominus$. They are prepared by (A) reacting by contacting $HOCH_2CH_2NH_3^\oplus HSO_4^\ominus$ with $^\oplus NH_3CH_2CH_2O\text{---}SO_3^\ominus$ in the presence of a catalytic amount of sulfuric acid at a temperature greater than about 140° C, thereby forming a reaction product comprising $O\text{-}(CH_2CH_2NH_3^\oplus)_2 \cdot 2HSO_4^\ominus$; and (B) reacting by contacting the reaction product of step (A) or $O\text{-}(CH_2CH_2NH_3^\oplus)_2 \cdot 2HSO_4^\ominus$ with a methanol solution of $HOCH_2CH_2NH_2$, thereby forming $O\text{-}(CH_2CH_2NH_3^\oplus)_2 SO_4^\ominus$ as a solid precipitate. The latter compound is extremely useful as a chemical intermediate in forming bis(2-aminoethyl) ether.

28 Claims, 3 Drawing Figures

NOVEL BISULFATE AND SULFATE SALTS OF BIS(2-AMINOETHYL) ETHER AND METHODS OF PREPARATION

BACKGROUND OF THE INVENTION

1. Field of the Invention

This invention pertains to new sulfate and bisulfate salts of bis(2-aminoethyl) ether, methods of their preparation, and their use in forming bis(2-aminoethyl) ether, hereinafter also referred to as BAEE. BAEE has the structural formula of $NH_2CH_2CH_2OCH_2CH_2NH_2$, or written in a more condensed form, $O-(CH_2CH_2NH_2)_2$.

2. Description of the Prior Art

Sulfuric acid has been heretofore reacted with ethanolamine ($HOCH_2CH_2NH_2$) to form hydroxyethyl ammonium bisulfate ($HOCH_2CH_2NH_3^\oplus HSO_4^\ominus$). This bisulfate has subsequently been heated at elevated temperatures to effect dehydration and thereby form 2-aminoethyl sulfate ($^\oplus NH_3CH_2CH_2O-SO_3^\ominus$). See, for example, Frankel et al. Ber., 51, 1660 (1918); Rollins et al., J. Am. Chem. Soc. 60, 2751 (1938); Gabriel, Ber. 21,1056, 2667 (1888); and Goldstein et al., USP 3,194,826 (July 13, 1965). In other reactions, alkylenimines have been produced from alkanolamines and sulfuric acid. British patent 962,866 and Wenker, J. Am Chem. Soc. 57, 2328 (1935).

SUMMARY OF THE INVENTION

It has now been discovered that the novel compound $O-(CH_2CH_2NH_3^\oplus)_2 \cdot SO_4^{\ominus\ominus}$, can be prepared in the novel process comprising the steps of:

(A) Reacting by contacting $HOCH_2CH_2NH_3^\oplus \cdot HSO_4^\ominus$ with $^\oplus NH_3CH_2CH_2O-SO_3^\ominus$ in the presence of a catalytic amount of sulfuric acid at a temperature greater than about 140° C, thereby forming a reaction product comprising $O-(CH_2CH_2NH_3^\oplus)_2 \cdot 2HSO_4^\ominus$, (which is likewise a new compound); and (B) Reacting by contacting the reaction product from step (A), or $O-(CH_2CH_2NH_3^\oplus)_2 \cdot 2HSO_4^\ominus$ per se, with a solution of methanol and a base which causes $O-(CH_2CH_2NH_3^\oplus)_2 \cdot SO_4^{\ominus\ominus}$ to form as a solid and selectively precipitate.

The base in step (B) should be ethanolamine when the filtrate is to be recycled back into Step A.

$O-(CH_2CH_2NH_3^\oplus)_2 \cdot SO_4^{\ominus\ominus}$ reacts readily with base to form bis(2-aminoethyl) ether, $O-(CH_2CH_2NH_2)_2$, which is a known compound having many utilities among which is gas conditioning. See British Pat. No. 863,242.

Step (A) itself is a new process in and of itself.

The combination of Steps (A) and (B) along with reaction of $O-(CH_2CH_2NH_3^\oplus)_2 \cdot SO_4^{\ominus\ominus}$ with base is a new process for making bis(2-aminoethyl) ether.

A further new process is to utilize the filtrate left from Step (B) as reactants for Step (A). All the filtrate can thus be continuously recycled. To do this, the base used in Step (B) must be ethanolamine present in a molar amount sufficient to replace the molar equivalents of ethanolamine removed from the reaction mixture by the precipitation of the $O-(CH_2CH_2NH_3^\oplus)_2 \cdot SO_4^{\ominus\ominus}$, i.e. two moles of ethanolamine per mole of $O-(CH_2CH_2NH_3^\oplus)_2 \cdot SO_4^{\ominus\ominus}$. Further to utilize this filtrate, or mother liquor, as the reactants for Step (A), the methanol should be removed by a process such as distillation, and sulfuric acid should be added to the filtrate, or mother liquor, in a molar amount equal to the moles of sulfate removed from the filtrate by the precipitation and removal of $O-(CH_2CH_2NH_3^\oplus)_2 SO_4^{\ominus\ominus}$ from the mixture. In any event there must be enough sulfuric acid present to provide the catalytic amount of $H_2SO_4$ needed for the reaction of Step (A). The make-up acid can be added first and the methanol removed second before returning the mother liquor constituents to Step (A) as the reactants.

Another variation of the process is to make bis(2-aminoethyl) ether, $O-(CH_2CH_2NH_2)_2$, directly from the reaction mixture of Step (A) above by adding base such as NaOH, KOH, $NH_3$, $CaCO_3$ or mixtures thereof, to the reaction mixture in a amount sufficient to substantially free all the amines in the reaction mixture, including those from the bisulfate salt of bis(2-aminoethyl) ether, $O-(CH_2CH_2NH_3^\oplus)_2 \cdot 2HSO_4^\ominus$.

Ethanolamine and a molar excess of sulfuric acid can be substituted in the above processes in which $HOCH_2CH_2-NH_3^\oplus HSO_4^\ominus$ and $^\oplus NH_3CH_2CH_2O-SO_3^\ominus$ and sulfuric acid are used as the initial reactants for Step (A). A molar excess of sulfuric acid means molar excess with respect to the ethanolamine.

DESCRIPTION OF THE INVENTION

Step (A)

Figure 1:
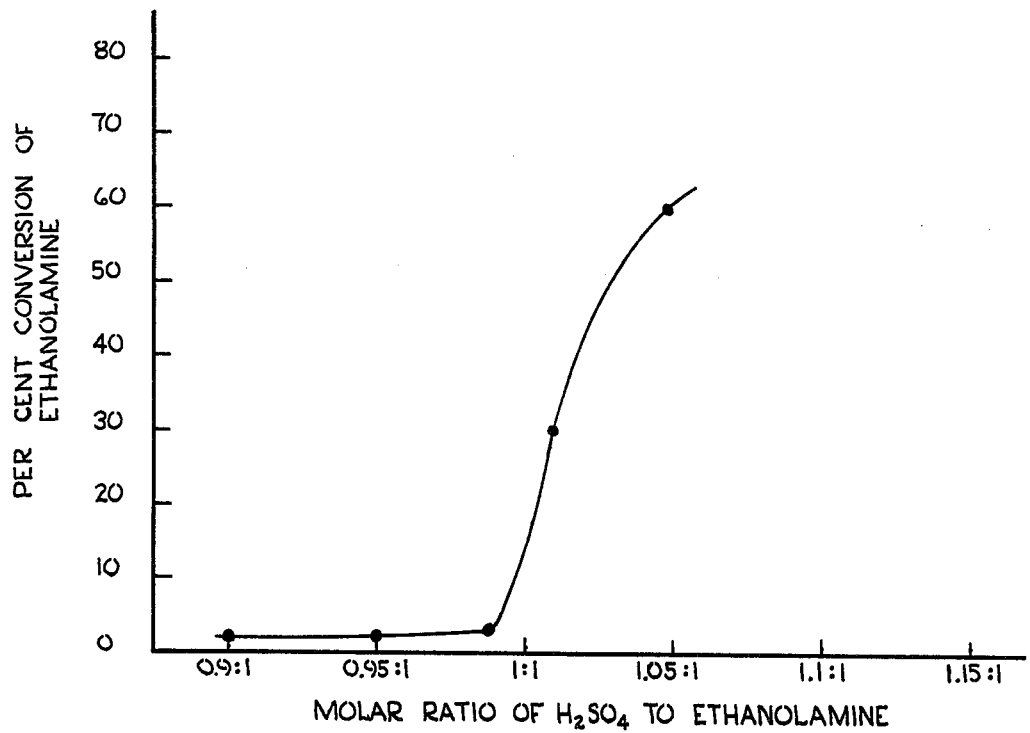
FIG. 1 is a graph of data points taken from Table I showing the sharp increase occurring in the conversion of ethanolamine to the bisulfate salt of bis(2-aminoethyl) ether, $O-(CH_2CH_2NH_3^\oplus)_2 \cdot 2HSO_4^\ominus$, when the molar ratio of sulfuric acid becomes greater than 1:1 with respect to ethanolamine when these two reactants are used as the initial reactants in Step (A).

Step (a), as described in the Summary above, is conducted by warming the reactants at an elevated temperature above about 140° C until the product is formed. Normally, satisfactory reaction rates have been achieved at temperatures of above about 165°, but preferred rates of reaction have been observed at temperatures of from about 180° to about 250° C. The reactants is step (A) are known compounds prepared by known techniques.

Alternatively, and preferably, the reactants are formed in situ by warming a mixture of ethanolamine and sulfuric acid to the reaction temperature set forth above. In this in situ procedure, sulfuric acid is present in the mixture in a molar excess, relative to ethanolamine, and catalyzes the reaction. Water is generated during the course of reaction and can be removed, in part, during the course of reaction. But at least some water must be present in the reaction mixture or else substantially the only product produced is $^\oplus NH_3CH_2CH_2O-SO_3^\ominus$. Thus we prefer to leave some or all of the water generated in the reaction mixture. Leaving sufficient water in the reaction mixture to form the desired product in commercial quantities necessitates conducting the reaction under superatmospheric, or autogenous pressures, or under reflux. The reaction is generally conducted under a blanket of an inert gas (e.g. nitrogen) to minimize oxidation of the organic reactants at such elevated temperatures, but an inert blanket is not necessary. The reaction mixture resulting from step (A) comprises the compound O—$(CH_2CH_2NH_3^{\oplus})_2 \cdot 2HSO_4^{\ominus}$ and can be used directly in step (B). Alternatively, the compound O—$(CH_2CH_2NH_3^{\oplus})_2 \cdot 2HSO_4^{\ominus}$ can be used per se in step (B).

It should be pointed out that in mixing the preferably initial reactants, ethanolamine and sulfuric acid, it is desirable to maintain a molar excess of sulfuric acid with respect to the ethanolamine throughout the mixing, although it is not absolutely necessary to do so. When ethanolamine and sulfuric acid react without being in the presence of a molar excess of sulfuric acid, side reactions occur forming products which involve displacement of hydroxyl by amine nitrogen.

This formation of these by products can be significantly reduced by keeping the reaction mixture cool during the time the reaction mixture has a molar excess of ethanolamine.

Once a molar excess of sulfuric acid is present, the reaction mixture can then be reacted as before, i.e. it can be heated and allowed to react at a temperature greater than about 140° C while maintaining at least some water in the reaction mixture.

To demonstrate the importance of having a molar excess of sulfuric acid present with respect to the ethanolamine when these two compounds were used as the initial reactants for Step (A) of the process, several comparative runs were made varying only the molar ratio of sulfuric acid to ethanolamine. The percent conversion of the ethanolamine to the bisulfate salt of bis-(aminoethyl) ether, i.e. O—$(CH_2CH_2NH_3^{\oplus})_2 \cdot 2HSO_4^{\ominus}$, was measured for each run. A very dramatic change from virtually no conversion to a very high conversion of the ethanolamine to the bisulfate salt of the ether was observed as the molar ratio of the acid to the ethanolamine was changed from only slightly less than 1:1 to only slightly more than 1:1. This change can be seen in Table I below. Data from Table I are plotted in FIG. 1 of the drawing for clearer illustration.

TABLE I

| Run Number | $H_2SO_4$/ Ethanolamine Mole Ratio | Percent Conversion of Ethanolamine to BAEE bisulfate salt |
| --- | --- | --- |
| 1 | 0.90 to 1.00 | 1.4 |
| 2 | 0.95 to 1.00 | 0.9 |
| 3 | 0.99 to 1.00 | 3.7 |
| 4 | 1.01 to 1.00 | 31.0 |
| 5 | 1.05 to 1.00 | 60.0 |

The preparation procedure for generating the above information is given below in Step 1-6, the ratio of the sulfuric acid to the ethanolamine was the only independent variable changed. This change is given for each run in the second column of Table I. The procedure was substantially as follows for each run.

1. Concentrated sulfuric acid (96%) was added to a one liter, 3-neck glass flash altered to contain a joint for a ground glass thermometer. The flask was equipped with an addition funnel, mechanical stirrer, water condenser, and a thermometer.

2. The stirrer was turned on at a fast rate. Ethanolamine was added dropwise to the sulfuric acid, in a nitrogen atmosphere, at a rate of about 10 ml/min. The temperature of the pot solution was allowed to rapidly rise until the temperature approached 200° C. The addition rate of the ethanolamine was adjusted to maintain a pot temperature under 200° C. As ethanolamine was continued to be added the solution began to reflux and the pot temperature slowly fell to about 160° C. at which temperature all the ethanolamine had been added. The amount of ethanolamine added in each run was constant (6.0 gram-moles).

3. The addition funnel and water condenser were removed and replaced with a distillation head and glass stopper. The flask was then equipped with a heating mantle. This mantle was connected to an electronic temperature controller which was attached to the thermometer inserted in the reaction flask. The temperature controller was set at 215° C maximum, the heating mantle and stirrer turned on, and about 75 ml. water was distilled from the flask. Distillation began at a pot temperature of about 160° C and was stopped at about 215° C.

4. The distillation head was then replaced by a water condenser. The reaction mixture in the flask was then heated under reflux conditions at about 215° C for about 90 minutes in a nitrogen atmosphere.

5. Samples were then taken, neutralized with 2 normal KOH, and analyzed using a gas chromatograph to determine the amount of conversion of the ethanolamine to the bisulfate salt of the bis(2-aminoethyl) ether.

The results for each run are given above in Table I and graphed on FIG. 1.

Regarding the need to maintain at least some water in the reaction mixture during Step (A), when sulfuric acid and ethanolamine have been used as the initial reactants, it is well known, as indicated by, inter alia, the references cited above in the "Background of the Invention", that when reacting sulfuric acid with ethanolamine to produce the product 2-aminoethyl hydrogen sulfate, $^{\oplus}NH_3CH_2CH_2O-SO_3^{\ominus}$, water is produced. Further it is known that the conversion of the ethanolamine to 2-aminoethyl hydrogen sulfate is increased by removing more water from the reaction mixture by methods such as evaporation by boiling.

It has not been known, however, that by retaining at least some free water in the reaction mixture, while heating it at a temperature greater than about 140° C, that the bisulfate salt of bis(2-aminoethyl) ether would be formed. That is it would be formed if in addition to the water retention limitation the additional limitation of using sulfuric acid in molar excess with respect to the ethanolamine was observed for the reaction. The amount of water retained is not critical insofar as making at least some BAEE bisulfate by this process. However it has been observed that the amount of water retained in the reaction mixture affects the reaction rate and the conversion of the ethanolamine to BAEE bisulfate salt. Large amounts of water tend to slow the reaction. Retention of only very small amounts of water reduces the conversion. Acceptable molar amounts of water retained with respect to the ethanolamine range from about 10:1, or even greater, to about 0.1:1. More acceptable molar amounts of water retained to ethanolamines used range from about 5:1 to about 0.2:1, with the preferred molar ratio being from about 3:1 to about 0.3:1. The molar amount of water retained described above is the sum of any moles of free water introduced into the reaction mixture, such as the water associated with aqueous sulfuric acid, plus all the moles of water which would be produced if the following assumed esterification reactions were driven to completion: $H_2SO_4 + NH_2CH_2CH_2OH \rightarrow HOCH_2CH_2NH_3^{\oplus} \cdot HSO_4^{\ominus} + {}^{\oplus}NH_3CH_2CH_2O-SO_3^{\ominus} + H_2O \rightarrow {}^{\oplus}NH_3CH_2CH_2O-SO_3^{\ominus} + H_2O$. Thus it can be seen that in speaking of retaining water in the process of this invention, that water does not have to come from free water. It can include water of esterification.

In using sulfuric acid and ethanolamine as the reactants in Step (A) of the process of this invention, it is often preferable not to retain all the water in the reaction mixture while the BAEE bisulfate is being formed. Particularly is it not preferable when operating at atmospheric pressure (however some water must be retained). During the step of heating these reactants to produce the bisulfate salt of BAEE, water can be retained in the reaction mixture by methods such as refluxing or operating under pressures greater than atmospheric. Following the step of producing the BAEE bisulfate salt, it is highly desirable to add water to the reaction mixture in sufficient quantity to hydrolyze the residual $^{\oplus}NH_3CH_2CH_2O-SO_3^{\ominus}$ (hereinafter also referred to as AEHS) to $HOCH_2CH_2NH_3^{\oplus}HSO_4^{\ominus}$ (hereinafter also referred to as HEAHS). This hydrolysis step is preferable whether or not some water was removed from the reaction mixture, or whether or not the BAEE bisulfate salt production step was carried out at atmospheric pressure. The purpose of the hydrolysis step is to make possible the isolation of the BAEE sulfate salt in Step (B) from the reaction mixture by its selective precipitation in the methanol solution of ethanolamine. It has been found that AEHS is insoluble in the methanol solution but that HEAHS is not. Since BAEE sulfate salt has also been found to be insoluble in methanol, it was discovered that by hydrolyzing the AEHS to HEAHS, the BAEE bisulfate forms and selectively precipitates upon addition of the reaction mixture to a methanol solution of ethanolamine. Selective precipitation is defined as meaning BAEE sulfate of at least 90% purity precipitates.

The reaction time for Step (A) is not critical. It will depend on variables such as the temperature at which the reaction is carried out. In one run wherein a 17% excess of sulfuric acid with respect to the ethanolamine, with the reaction temperature being maintained at 216° C, there was obtained a 35% conversion after 0.2 hours, a 44% conversion after 0.3 hour, and 50% conversion after 0.8 hour. On the other hand for a reaction carried out at a temperature of 175° C wherein the molar excess of acid used was 15%, there was obtained only a 24% conversion of the ethanolamine to the bisulfate salt of bis(2-aminoethyl) ether after 1.3 hours; a 32% conversion after 2.3 hours; a 41% conversion after 3.8 hours; and a 60% conversion after 31 hours.

The effect of running the reaction of Step (A) at lower temperatures in an autoclave upon reaction time is demonstrated for a specific reaction time, 16 hours, in Table II. In each run, ethanolamine was added to an autoclave containing a molar excess of sulfuric acid with respect to the ethanolamine. The autoclave was sealed, immersed in a hot bath, and heated at a constant temperature for 16 hours at autogeneous pressures. For each run the temperature was varied, and the percent of the ethanolamine converted to the product, bisulfate salt of bis(aminoethyl) ether measured.

TABLE II

| $H_2SO_4$ (moles) | Ethanolamine (moles) | Molar Excess of $H_2SO_4$ % | Reaction Temperature ° C | % Ethanolamine Converted to the bisulfate salt |
|---|---|---|---|---|
| 0.1668 | 0.1383 | 20.6 | 110° | None detected |
| 0.083 | 0.069 | 20.3 | 120° | None detected |
| 0.1667 | 0.1381 | 20.7 | 130° | None detected |
| 0.083 | 0.069 | 20.3 | 140° | 7.9 |
| 0.1668 | 0.1374 | 21.4 | 145° | 2.9 |
| 0.1668 | 0.1381 | 20.8 | 150° | 27.7 |
| 0.083 | 0.069 | 20.3 | 160° | 60.0 |
| 0.083 | 0.069 | 20.3 | 180° | 65.8 |

STEP (B)

Step (B) comprises reacting by contacting the reaction product from step (A), or $O-(CH_2CH_2NH_3^{\oplus})_2.2HSO_4^{\ominus}$ itself, with a methanol solution of base. This base can be practically any base which will react with sulfuric acid such as amines, ammonia, $CaCO_3$, KOH and NaOH. However, if the filtrate is going to be used for recycle then the base should be the ethanolamine. The amounts of the base to be used should be enough to approach neutralization, this neutralization converts the bisulfate salt of BAEE to the sulfate salt. The sulfate form of BAEE is insoluble in methanol and selectively precipitates out. If more ethanolamine is added than is removed as BAEE sulfate, there is an undesirable build-up of amine salts during a sequence of several recycles. Using too little ethanolamine as the base for a filtrate recycle process reduces the amount of $O-(CH_2CH_2NH_3^{\oplus})_2 SO_4^{\ominus\ominus}$ precipitated. Knowing in advance how much $O-(CH_2CH_2NH_3^{\oplus})_2 SO_4^{\ominus\ominus}$ is going to precipitate can be determined by trial and error for a given set of operating parameters of a recycle process. The result of step (B) is the formation of $O-(CH_2CH_2NH_3^{\oplus})_2 SO_4^{\ominus\ominus}$ as a solid precipitate. The reaction of the amine with acid is exothermic and will raise the temperature of the methanol solution to its maximum of about 67° C, which is the reflux temperature of the reaction mixture. At atmospheric pressure this reflux temperature is about 67° C. The order of addition is not critical, but we have found that best results are achieved when the reaction product from step (A), or $O-(CH_2CH_2NH_3^{\oplus})_2.2HSO_4^{\ominus}$, is added to a methanol solution of base, preferably a methanol solution of ethanolamine, instead of vice versa. The solid precipitate is easily recovered from the reaction mixture by conventional techniques, such as by filtration.

It was observed that $O-(CH_2CH_2NH_3^{\oplus})_2 SO_4^{\ominus\ominus}$ selectively precipitates from the reaction mixture in Step (B) and the product is obtained in essentially pure form. However, $^{\oplus}NH_3CH_2CH_2O-SO_3^{\ominus}$ also precipitates in methanol. Thus, we normally add water to the reaction product of Step (A) and heat the reaction mixture at an elevated temperature (e.g. from about 100° to about 130° C) for a time sufficient to convert most of the $^{\oplus}NH_3CH_2CH_2O-SO_3^{\ominus}$ back to $HOCH_2CH_2NH_3^{\oplus}HSO_4^{\ominus}$. We then use this "hydrolyzed" reaction mixture in Step (B). This step permits the selective precipitation of the BAEE sulfate.

The formation of BAEE is accomplished by contacting this BAEE sulfate salt with base. The stoichiometry of this reaction, of course, requires two equivalents of base per mole of BAEE sulfate salt. Any base that will release BAEE can be used in this reaction, but sodium hydroxide, potassium hydroxide, calcium carbonate, or ammonia are preferred, based on cost and availability. Ammonia is the most preferred base since ammonium sulfate precipitates easily from solution, is a commercial product itself, and excess ammonia is easily volatilized from the desired product.

Bis(2-aminoethyl) ether can also be produced by reacting bis(2-aminoethyl) ether bisulfate with base. This is less desirable, from a procedurial standpoint due to the difficulty in isolating the pure product from the reaction mixture.

Experimental

The following experimental detail will further illustrate the invention.

EXAMPLE 1

Ethanolamine (6.0 moles, 366.6 g, 361.2 ml) was added dropwise at a rate of about 10 ml per minute to a rapidly stirred aliquot of concentrated (96 percent) sulfuric acid (6.3 moles, 644 g. 350 ml) in a reaction vessel equipped with a mechanical stirrer, condenser, temperature recording means and an addition funnel containing a pressure equalizing arm. The temperature of the reaction mixture increased rapidly to about 200° C and thereafter the addition of ethanolamine was adjusted to maintain the pot temperature just under 200° C. As the addition of ethanolamine to the sulfuric acid progressed, the solution begins to reflux and the temperature slowly fell to about 160° C., The reaction mixture was placed in a distillation apparatus and warmed to 215° C with distillation of water from the reaction mixture beginning at a pot temperature of about 160° C and ending at about 215° C. The amount of water removed was approximately 76 ml. The reaction product was subsequently heated for an additional 90 minutes at 215° C under a nitrogen atmosphere; this produced a reaction product containing substantial amounts of $O—(CH_2CH_2NH_3^\oplus)_2.2HSO_4^\ominus$. This concludes Step (A) of the instant process.

The above reaction mixture from Step (A) was cooled to about 120° C and 130 ml of water added. The stirred reaction mixture was heated at 115° C for about 30 minutes and cooled. By this procedure, residual $^\oplus NH_3CH_2CH_2O—SO_3^\ominus$ was hydrolyzed to $HOCH_2CH_2NH_3^\oplus HSO_4^\ominus$.

The above "hydrolyzed" reaction mixture was then added to ethanolamine (168 g, 2.75 mols) dissolved in 2 liters of methanol, resulting in precipitation of a solid. The solid was recovered by filtration techniques, washed several times with methanol, and identified as $O—(CH_2CH_2NH_3^\oplus)_2 SO_4^{\ominus\ominus}$. The product, thus obtained, weighed approximately 275 g.

Methanol and some water were stripped from the mother liquor (from which the solid product was recovered), sulfuric acid added to the mother liquor and the "pot residue" thus obtained recycled back to the front end of the process. This means that the process can be conducted as a batch process or as a recycle, continuous process.

PREPARATION OF BIS(2-AMINOETHYL) ETHER $O—(CH_2CH_2NH_3^\oplus)_2 SO_4^{\ominus\ominus}$ from above was mixed with a stoichiometric amount of sodium hydroxide in methanol. From this mixture, bis(2-aminoethyl) ether was recovered by distillation at elevated temperature and atmospheric pressure as a clear, colorless liquid having a typical amine odor and a boiling point of 187° C at 760 mm Hg, a freezing point of −42.4° to −40.4° C and an index of refraction of 1.4562 at 25° C. The product was obtained in good yields.

EXAMPLE 2

Ethanolamine (0.5 mole) was added to sulfuric acid (0.575 mole) with cooling. When the addition was complete, the reaction mixture was heated in a sealed container at 190° C for sixteen hours. The reaction mixture was cooled and added to aqueous sodium hydroxide. Bis(2-aminoethyl)ether was thus produced in approximately 49 percent yield.

EXAMPLE 3

Four 1-liter flasks equipped with overflow sidearms were set up in series to allow a cascading flow of reaction mixture through the system. Flasks 1 and 2 were equipped with magnetic stirring means and distillation apparatus. Flasks 3 and 4 were equipped with mechanical stirrers and condensers.

Upon completion of the first cycle of the continuous process, liquid filtrate, obtained from the precipitation step of this example, was used as feed to Flask 1. To start this example an initial solution substantially representing the recycled filtrate was prepared and used as feed for the first cycle of the continuous process. The solution, consisting of, methanol (500 ml), concentrated sulfuric acid (181.6 g, 1.78 moles), ethanolamine (103.4 g, 1.69 moles) and water (29.9 g, 1.66 moles), was added at a rate of 720 ml per hour to flask 1 through the top of the distillation column. The pot temperature of the mixture in flask 1 was controlled at 130° C. Under these conditions, methanol distilled from the reaction mixture at the rate of approximately 500 ml per hour. The methanol was collected for recycle. The pot residue overflowed directly into flask 2 at a rate of approximately 307.5 g per hour.

The reaction mixture in flask 2 was maintained at a pot temperature of 215° C. Under these conditions, water distilled from the reaction mixture at a rate of 45.1g per hour. The water was collected for recycle in the hydrolysis step below. The pot residue overflowed directly into flask 3 at a rate of 262.4 g per hour.

The reaction mixture in flask 3 was heated at a pot temperature of 210° C and overflowed directly into flask 4 at a rate of 262.4 g per hour.

In flask 4 the reaction mixture was cooled to 130° C and blended with water which was added to flask 4 at a rate of 37.6 g per hour. The contents from flask 4 overflowed directly into a collecting container at a rate of 300.0 g per hour. The material collected is the hydrolyzed reaction product of Step (A)in the process.

An aliquot (1200g) of the material collected was blended with a solution of ethanolamine (165.6 g, 2.71 moles) in two liters of methanol. Bis(2-aminoethyl)ether sulfate (274 g, 1.36 moles) precipitated and was recovered by filtration. The liquid filtrate was collected and reacidified by blending with concentrated sulfuric acid (138.4 g, 1.36 moles). The reacidified filtrate was recycled as feed to flask 1.

Bis (2-aminoethyl) ether sulfate was produced at a rate of approximately 68.5 gms per hour for a continuous run of about 96 hours.

The bis(2-aminoethyl)ether was released by washing the filter cake twice with 180 ml portions of 19.0 weight percent (2 moles) of ammonia in methanol and twice with 180 ml portions of methanol. The combined liquid washes were collected and distilled under reduced pressure. This distillation removed methanol which was collected and recycled to the precipitation step above and the bis(2-aminoethyl)ether recovered as the pot residue. The ammonium sulfate remaining on the filter was likewise recovered and dried. Ammonium sulfate is an item of commerce and is a valuable by-product.

The new compound, $O-(CH_2CH_2NH_4^{\oplus})_2SO_4^{\ominus\ominus}$, referred to as the sulfate salt of bis(2-aminoethyl) ether, or referred to as 2,2'-oxybis(ethyl ammonium) sulfate, has the following properties. It is a white solid and has a molecular weight of approximately 202. When added to water it is neutral or slightly acid. When titrated with KOH it exhibits an endpoint pH of about 11, corresponding to the conversion of the amine sulfate to the free amine and $K_2SO_4$. It has no melting point, but rather starts to char at a temperature of about 285° C. In the following substances it has the solubilities given.

Figure 2:
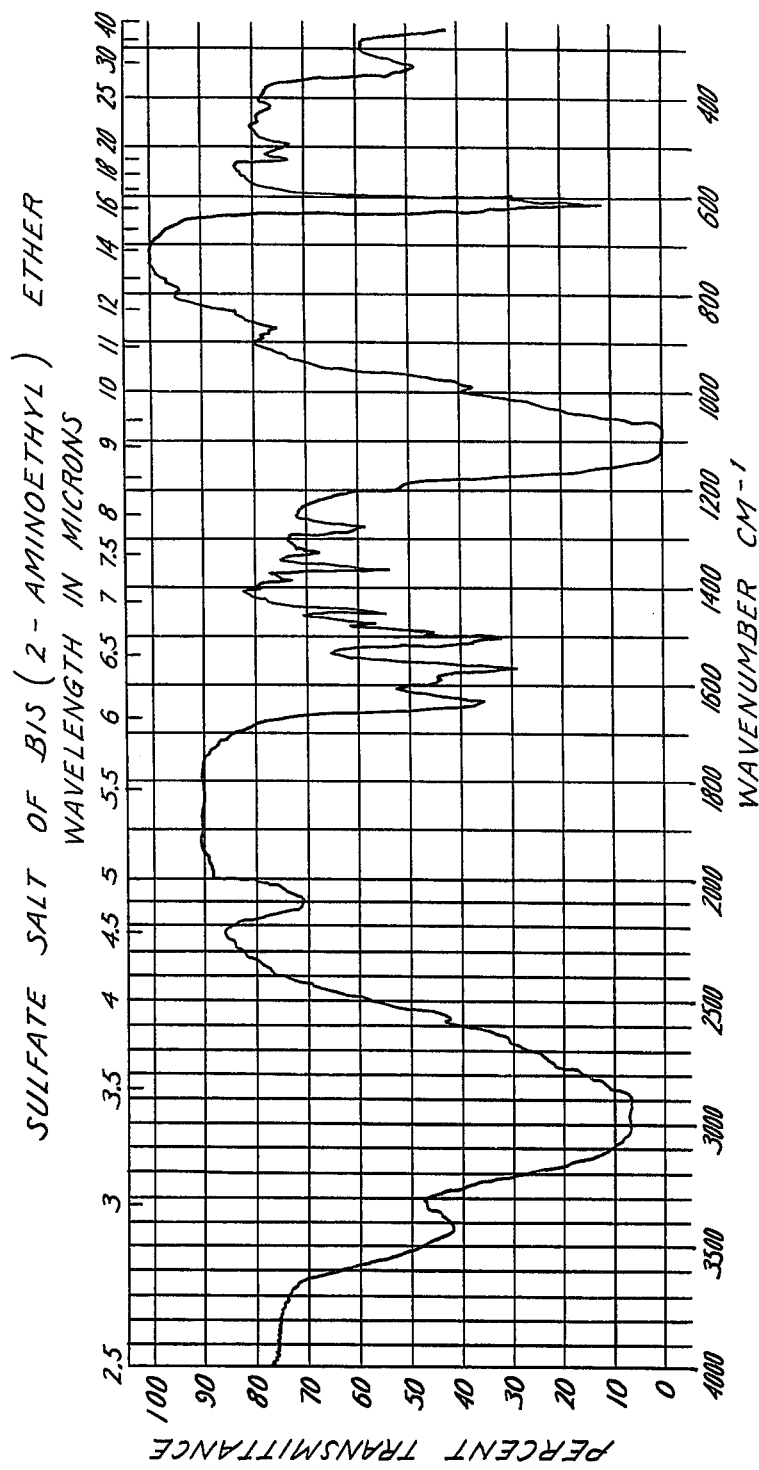
FIG. 2 is a tracing (draftsman's copy) of an infrared spectrograph of the sulfate salt of bis(2-aminoethyl) ether, $O-(CH_2CH_2NH_3^\oplus)_2 SO_4^{\ominus\ominus}$.

Water: soluble
Methanol: insoluble
Ethanol: insoluble
Diethyl ether: insoluble
Acetone: insoluble An infrared spectra is consistent with the structure of $O-(CH_2CH_2NH_3^{\oplus})_2 SO_4^{\ominus}$. A draftsmen's copy of this spectrum is given in FIG. 2.

Properties of this new compound of $O-(CH_2CH_2NH_3^{\oplus})_2.2HSO_4$ are as follows. It is a soft solid. It will readily absorb enough water from the air to become an oil. When titrated it exhibits the expected sharp endpoint corresponding to the free acid and then gives the amine endpoint at a pH of about 11. In the following substances it has the given solubilities.

Water: soluble
Ethanol: very slightly soluble
Methanol: slightly soluble
Diethyl ether: insoluble
Acetone: insoluble It should be pointed out that the $O-(CH_2CH_2NH_3^{\oplus})_2.2HSO_4$ for which the above properties were determined, was not taken directly from the reaction mixture of Step (A) above in which this compound is made because of separation problems involved in isolating it from the other liquid amines in this acidic reaction mixture. Rather it was made from some of the pure bis(2-aminoethyl) ether, $O-(CH_2CH_2NH_2)_2$, made by the process of this invention. A stoichiometric amount of sulfuric acid was reacted with this pure bis(2-aminoethyl) ether to form the bisulfate salt.

Figure 3:
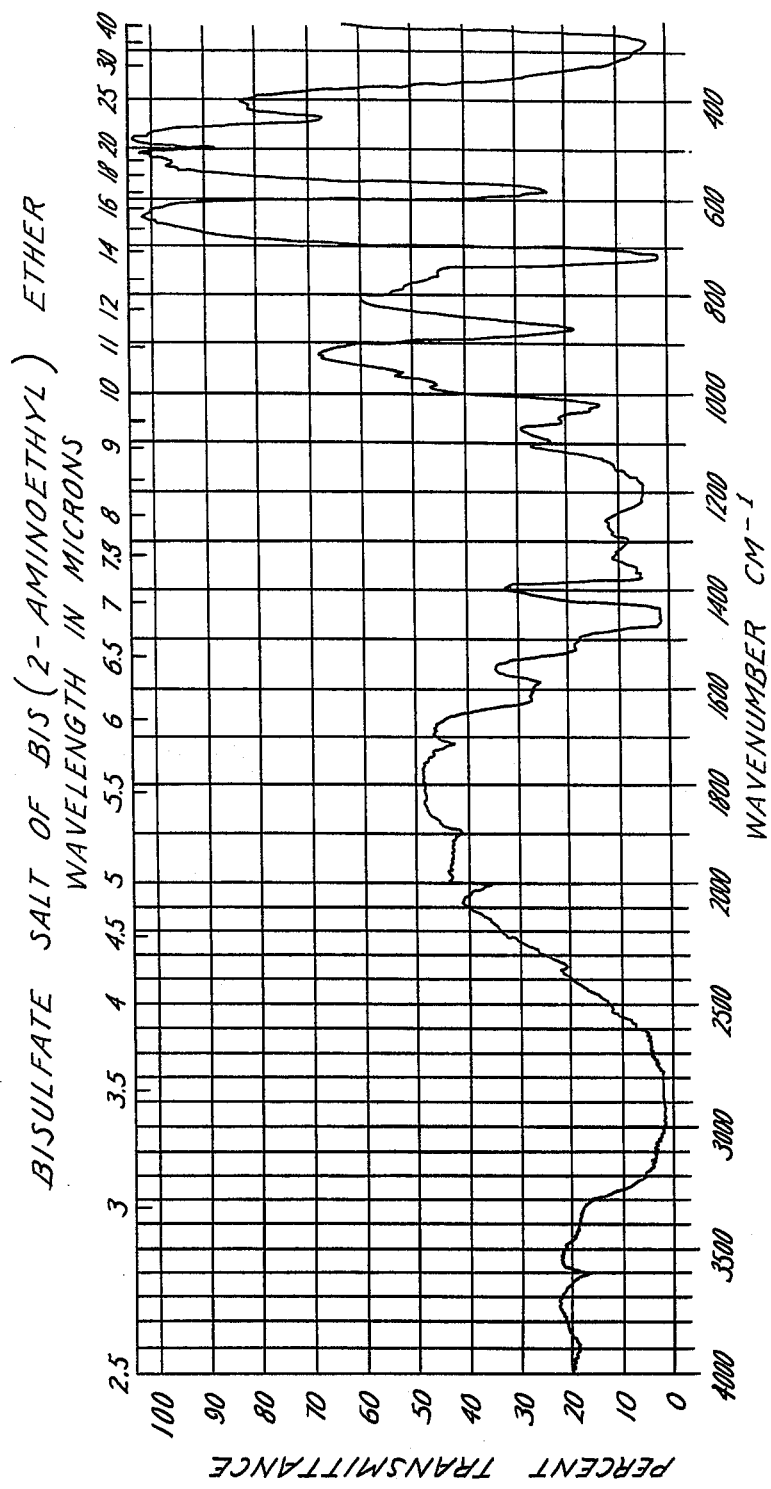
FIG. 3 is a tracing (draftsman's copy) of an infrared spectrograph of the bisulfate salt of bis(2-aminoethyl) ether, $O-(CH_2CH_2NH_3^\oplus)_2 \cdot 2HSO_4^\ominus$.

An infrared spectra is consistant with the structure $O-(CH_2CH_2NH_3^{\oplus})_2.2HSO_4^{\ominus}$. A draftsmen's copy of this spectrum is given in FIG. 3.

What is claimed is:

1. A process for preparing $O-CH_2CH_2NH_3^{\oplus})_2.2HSO_4^{\ominus}$ comprising reacting by contacting $HOCH_2CH_2NH_3^{\oplus}HSO_4^{\ominus}$ with $^{\oplus}NH_3CH_2CH_2OSO_3^{\ominus}$ in the presence of a catalytic amount of sulfuric acid at a temperature of at least about 140° C.

2. The process defined by claim 1 wherein $HOCH_2CH_2NH_3^{\oplus}HSO_4^{\ominus}$ and $^{\oplus}NH_3CH_2CH_2OSO_3^{\ominus}$ are generated in situ by reacting by contacting ethanolamine with sulfuric acid at a temperature of at least about 140° C while retaining at least some water in the reaction mixture, said sulfuric acid being present in the reaction mixture in a molar excess relative to the ethanolamine.

3. A process for preparing $O-(CH_2CH_2NH_3^{\oplus})_2.2SO_4^{\ominus\ominus}$ comprising (A) reacting by contacting $HOCH_2CH_2NH_3^{\oplus}HSO_4^{\ominus}$ with $^{\oplus}NH_3CH_2CH_2OSO_3^{\ominus}$ in the presence of a catalytic amount of sulfuric acid at a temperature of at least about 140° C thereby forming a reaction product comprising $O-(CH_2CH_2NH_3^{\oplus})_2.2HSO_4^{\ominus}$; and (B) reacting by contacting the reaction product of Step (A) with a methanol solution of base, thereby forming the product $O-(CH_2CH_2NH_3^{\oplus})_2SO_4^{\ominus\ominus}$ as a solid precipitate.

4. The process of claim 3 wherein the base in Step (B) is ethanolamine.

5. The process defined by claim 4 in which the reaction product of Step (A) is contacted with water to hydrolyze residual $^{\oplus}NH_3CH_2CH_2OSO_3^{\ominus}$ to $HOCH_2CH_2NH_3^{\oplus}HSO_4^{\ominus}$ prior to use in Step (B) so that in Step (B), the $O-(CH_2CH_2NH_3^{\oplus})_2SO_4^{\ominus}$ formed will selectively precipitate from the reaction product of Step (A).

6. The process defined by claim 5 which comprises the additional steps of:
   (1) separating the solid precipitate from the liquid mixture of step B;
   (2) removing methanol from the liquid mixture of (1) above and adding sulfuric acid to the liquid mixture in a molar amount substantially equal to the molar amount of $O-(CH_2CH_2NH_3^{\oplus})_2.SO_4^{\ominus\ominus}$ which precipitated out and was separated in step (1) above;
   (3) recycling the liquid remaining from step (2) back into step A, thereby forming a continuous process for making $O-(CH_2CH_2NH_3^{\oplus})_2SO_4^{\ominus\ominus}$.

7. The process defined by claim 4 wherein $HOCH_2CH_2NH_3^{\oplus}HSO_4^{\ominus\ominus}$ and $^{\oplus}NH_3CH_2CH_2OSO_3^{\ominus}$ in step (A) are generated in situ by reacting by contacting ethanolamine with sulfuric acid at a temperature of at least about 140° C, while retaining water in the reaction mixture, said sulfuric acid being present in the reaction mixture in a molar excess relative to the ethanolamine.

8. The process defined by claim 7 in which the reaction product of step (A) is contacted with water to hydrolyze residual $^{\oplus}NH_3CH_2CH_2OSO_3^{\ominus}$ to $HOCH_2CH_2NH_3^{\oplus}HSO_4^{\ominus}$ prior to use in step (B).

9. The process defined by claim 8 which comprises the additional steps of:
   (1) separating the solid precipitate from the liquid mixture of step (B)
   (2) adding sulfuric acid to the liquid mixture remaining from step (1) in an amount such that the molar ratio of sulfuric acid added to the ethanolamine of the methanol solution of ethanolamine added in step (B) above is at least 1:1,
   (3) removing methanol from the acidified liquid mixture; and
   (4) recycling the liquid remaining from step (3) back into step (A), thereby forming a continuous process for making $O-(CH_2CH_2NH_3^{\oplus})_2SO_4^{\ominus\ominus}$.

10. The process defined by claim 5 wherein the solid precipitate is separated from the liquid mixture of step (B) and reacted with base to form bis(2-aminoethyl) ether.

11. The process defined by claim 10 wherein said base is sodium hydroxide, potassium hydroxide, ammonium hydroxide or ammonia.

12. A process for producing $O-(CH_2CH_2NH_3^{\oplus})_2.2HSO_4^{\ominus}$ comprising reacting by contact a molar excess of sulfuric acid with ethanolamine at a temperature greater than about 140° C while retaining water in the reaction mixture.

13. The process of claim 12 wherein the reaction is carried out at a temperature greater than about 165° C., and wherein the water retained has a molar ratio with respect to the ethanolamine used of from about 10:1 to about 0.1:1.

14. The process of claim 12 wherein the reaction is carried out at a temperature of from about 180° C to about 250° C., and wherein the water retained has molar ratio with respect to the ethanolamine used of from about 5:1 to about 0.2:1.

15. A process for producing O—(CH$_2$CH$_2$NH$_2$)$_2$ comprising:
   (a) reacting a molar excess of sulfuric acid sulfuric acid with ethanolamine at a temperature greater than about 140° C while retaining water in the reaction mixture; and
   (b) adding a base to the reaction mixture which will release free bis (2-aminoethyl)ether from the reaction mixture.

16. The process of claim 15 wherein the reaction in step (a) is carried out at a temperature greater than about 165° C and the base used in step (b) is selected from the group consisting of amines, ammonia, sodium hydroxide, potassium hydroxide, ammonium hydroxide, calcium carbonate, and mixtures thereof.

17. A process for making O—(CH$_2$CH$_2$NH$_3^{\oplus}$)$_2$SO$_4^{\ominus\ominus}$ comprising:
   (a) reacting by contact a molar excess of sulfuric acid with ethanolamine at a temperature greater than about 140° C while retaining some water in the reaction mixture;
   (b) forming a solid precipitate of O—(CH$_2$CH$_2$NH$_3^{\oplus}$)$_2$SO$_4^{\ominus\ominus}$ by reacting the reaction mixture of Step (a) with a methanol solution of base.

18. The process of claim 17 wherein the base in Step (b) is ethanolamine.

19. The process of claim 18 wherein the reaction of Step (a) is carried out at a temperature greater than about 165° C.

20. The process of claim 18 wherein the reaction of Step (a) is carried out at a temperature of from about 180° C to about 250° C., while the water retained has a molar ratio with respect to the ethanolamine used of from about 3:1 to about 0.3:1.

21. A process for the production of O—(CH$_2$CH$_2$NH$_2$)$_2$ comprising:
   (a) reacting by contact a molar excess of sulfuric acid with ethanolamine at a temperature greater than about 140° C while retaining some water in the reaction mixture, said reaction mixture containing reaction products including O—(CH$_2$CH$_2$NH$_3^{\oplus}$)$_2$.2HSO$_4^{\ominus}$ and $^{\oplus}$NH$_3$CH$_2$CH$_2$O—SO$_3^{\ominus}$;
   (b) adding water to the reaction mixture in sufficient quantity to substantially hydrolyze all the $^{\oplus}$NH$_3$CH$_2$CH$_2$O—SO$_3^{\ominus}$ to HOCH$_2$CH$_2$NH$_3^{\oplus}$·HSO$_4^{\ominus}$;
   (c) forming a precipitate of O—(CH$_2$CH$_2$NH$_3^{\oplus}$)$_2$SO$_4^{\ominus\ominus}$ by reacting the reaction mixture of Step (B) with a methanol solution of base,
   (d) separating the precipitate O—(CH$_2$CH$_2$NH$_3^{\oplus}$)$_2$SO$_4^{\ominus\ominus}$ from the reaction mixture of Step (c);
   (e) treating the O—(CH$_2$CH$_2$NH$_3^{\oplus}$)$_2$ SO$_4^{\ominus\ominus}$ with a base which will release free bis (2-aminoethyl)ether and form the sulfate salt of the base.

22. The process of claim 21 wherein the base used in the methanol solution of step (c) is ethanolamine so that the O—(CH$_2$CH$_2$NH$_3^{\oplus}$)$_2$SO$_4^{\ominus\ominus}$ which is formed will selectively precipitate from the reaction mixture while leaving the filtrate capable of being recycled back into step (a) following the removal of the methanol from the filtrate accompanied by the addition of sufficient sulfuric acid to the filtrate to make up for the sulfate lost from the filtrate by the selective precipitation of the O—(CH$_2$CH$_2$NH$_3^{\oplus}$)$_2$SO$_4^{\ominus\ominus}$.

23. The process of claim 22 wherein the reaction in step (a) is carried out at a temperature above about 165° C and the base used in step (e) is selected from the group consisting of NaOH, KOH, NH$_3$, CaCO$_3$ and mixtures thereof.

24. The process of claim 22 wherein the reaction of step (a) is carried out at temperature of from about 180° C to about 250° C., and wherein the water retained in Step (a) has a molar ratio with respect to the ethanolamine of from about 3:1 to about 0.2:1.

25. A recycle process for the preparation of bis(2-aminoethyl)ether, O—(CH$_2$CH$_2$NH$_2$)$_2$, comprising:
   (a) reaction by contact a molar excess of sulfuric acid with ethanolamine at a temperature greater than about 140° C while retaining at least some water in the reaction mixture, said reaction mixture containing reaction products including bis (2-aminoethyl)ether bisulfate and $^{\oplus}$NH$_3$CH$_2$CH$_2$O—SO$_3^{\ominus}$;
   (b) adding water to the reaction mixture in sufficient quantity to substantially hydrolyze the $^{\oplus}$NH$_3$CH$_2$CH$_2$O—SO$_3^{\ominus}$ to HOCH$_2$CH$_2$NH$_3^{\oplus}$·HSO$_4^{\ominus}$;
   (c) forming a precipitate of O—(CH$_2$CH$_2$NH$_3^{\oplus}$)$_2$SO$_4^{\ominus\ominus}$ by reacting the reaction mixture of step (b) with a methanol solution of ethanolamine where the molar amount of ethanolamine of the methanol solution of ethanolamine is substantially equivalent to twice the molar amount of O—(CH$_2$CH$_2$NH$_3^{\oplus}$)$_2$ SO$_4^{\ominus\ominus}$ precipitated out;
   (d) separating the precipitate, O—(CH$_2$CH$_2$NH$_3^{\oplus}$)$_2$SO$_4^{\ominus\ominus}$, from the remaining liquor;
   (e) reacting by contact the O—(CH$_2$CH$_2$NH$_3^{\oplus}$)$_2$ SO$_4^{\ominus\ominus}$ with a base to form a reaction product comprising O—(CH$_2$CH$_2$NH$_2$)$_2$ and the sulfate salt of the base; and
   (f) taking the remaining mother liquor of step (d) above and:
      (1) adding to it sulfuric acid in a molar amount substantially equal to the moles of O—(CH$_2$CH$_2$NH$_3^{\oplus}$)$_2$ SO$_4^{\ominus\ominus}$ precipitated in step (c) above and removed in step (d) above;
      (2) distilling off the methanol from this mother liquor; and
      (3) returning this mother liquor to step (a) of the process above where its components replace the sulfuric acid and ethanolamine as the reactants for the remaining cycles of the process which are to be reacted, as in step (a), at a temperature greater than about 140° C while retaining water in the reaction mixture, and having a catalytic amount of sulfuric acid present; and
   (g) separating the O—(CH$_2$CH$_2$NH$_2$)$_2$ formed in step (c) above from the sulfate salt of the base formed.

26. The process of claim 25 wherein
   the reactions in steps (a) and (f-3) are carried out at temperatures from about 165° C to about 250° C, and the base of step (e) is selected from a group consisting of ammonia, ammonium hydroxide, sodium hydroxide, potassium hydroxide, and mixtures thereof.

27. The process of claim 25 wherein the methanol distillation step of step (f-2) and the sulfuric addition step of step (f-1) are sequentially reversed.

28. The process of claim 25 wherein the base used in step (e) is selected from a group consisting of ammonia, amines, NaOH, KOH and CaCO$_3$.

* * * * *

UNITED STATES PATENT AND TRADEMARK OFFICE
CERTIFICATE OF CORRECTION

PATENT NO. : 4,083,873

DATED : April 11, 1978

INVENTOR(S) : Fred A. Sherrod and Bobby R. Ezzell

It is certified that error appears in the above-identified patent and that said Letters Patent are hereby corrected as shown below:

On the title page under References Cited, add -- Wagner, et al, <u>Synthetic Organic Chemistry</u>, pp. 230-231 (1953).--

On the title page, the formula bridging the second and third lines of the Abstract should appear as follows:

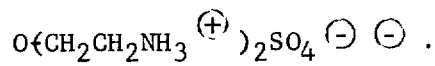

On the title page, the last formula given in the abstract should appear as follows:

Column 1, line 19, "from" should be --form--.

Column 2, line 48, "is step (A)" should be --in step (A)--.

Column 3, line 7, "preferably" should be --preferable--.

Column 3, line 57, "flash" should be --flask--.

Column 9, line 23, the second "of" should be deleted.

UNITED STATES PATENT AND TRADEMARK OFFICE
CERTIFICATE OF CORRECTION

PATENT NO. : 4,083,873

DATE : April 11, 1978

INVENTOR(S) : Fred A. Sherrod and Bobby R. Ezzell

It is certified that error appears in the above-identified patent and that said Letters Patent are hereby corrected as shown below:

Column 9, lines 24 and 36, the formula " $O(CH_2CH_2NH_3 \oplus)_2 \cdot 2HSO_4$ " should be -- $O(CH_2CH_2NH_3 \oplus)_2 \cdot 2HSO_4 \ominus$ --.

Column 9, line 46, "consistant" should be --consistent--.

Column 9, line 46, --of-- should follow "structure".

Column 9, lines 50-51, (Claim 1), the formula, " $O-CH_2CH_2NH_3 \oplus)_2 \ 2HSO_4 \ominus$ " should be -- $O(CH_2CH_2NH_3 \oplus)_2 \cdot 2HSO_4 \ominus$ --.

Column 9, lines 63-64, (Claim 3), the formula, " $O(CH_2CH_2NH_3 \oplus)_2 \cdot 2SO_4 \ominus\ominus$ " should appear as -- $O(CH_2CH_2NH_3 \oplus)_2 \cdot SO_4 \ominus \ominus$ --.

Column 10, line 11, (Claim 5), the formula, " $\oplus NH_3CH_2CH_2OSO_3 \oplus$ ", should be -- $\oplus NH_3CH_2CH_2OSO_3 \ominus$ --.

Column 10, line 13, (Claim 5), " $O(CH_2CH_2NH_3 \oplus)_2 SO_4 \ominus$ " should be -- $O(CH_2CH_2NH_3 \oplus)_2 SO_4 \ominus \ominus$ --.

Column 10, line 29, (Claim 7), " $HOCH_2CH_2NH_3 \oplus HSO_4 \ominus \ominus$ " should be -- $HOCH_2CH_2NH_3 \oplus HSO_4 \ominus$ --.

UNITED STATES PATENT AND TRADEMARK OFFICE
CERTIFICATE OF CORRECTION

PATENT NO.  : 4,083,873

DATED       : April 11, 1978

INVENTOR(S) : Fred A. Sherrod and Bobby R. Ezzell

It is certified that error appears in the above-identified patent and that said Letters Patent are hereby corrected as shown below:

Column 11, lines 10-11, (Claim 15), the second "sulfuric acid" should be deleted.

Column 12, line 16, (Claim 25), "reaction" should be changed to --reacting--.

Signed and Sealed this

Twenty-first Day of November 1978

[SEAL]

Attest:

RUTH C. MASON
*Attesting Officer*

DONALD W. BANNER
*Commissioner of Patents and Trademarks*